United States Patent [19]

Lukens, Jr. et al.

[11] 4,353,886
[45] Oct. 12, 1982

[54] METHOD FOR DETECTING ORGANIC VAPORS

[75] Inventors: Herbert R. Lukens, Jr.; Colin B. Williams, both of La Jolla, Calif.

[73] Assignee: IRT Corporation, San Diego, Calif.

[21] Appl. No.: 146,476

[22] Filed: May 5, 1980

[51] Int. Cl.³ .......................................... G01N 33/00
[52] U.S. Cl. ...................................... 424/1; 23/230 B; 422/83; 424/8; 424/12
[58] Field of Search ............... 424/1, 12, 8; 23/230 B; 422/83, 84

[56] References Cited

U.S. PATENT DOCUMENTS

| | | | |
|---|---|---|---|
| 3,960,489 | 6/1976 | Giaever | 424/12 X |
| 3,979,184 | 9/1976 | Giaever | 23/230 B |
| 4,011,308 | 3/1977 | Giaever | 424/12 X |
| 4,011,350 | 3/1977 | Markovits et al. | 427/2 |
| 4,019,864 | 4/1977 | Saito et al. | 422/83 |
| 4,050,895 | 9/1977 | Hardy et al. | 23/230 B X |
| 4,054,646 | 10/1977 | Giaever | 424/12 |
| 4,169,138 | 9/1979 | Jonsson | 424/12 |
| 4,205,952 | 6/1980 | Cais | 23/230 B |

*Primary Examiner*—Christine M. Nucker
*Attorney, Agent, or Firm*—Fitch, Even, Tabin, Flannery & Welsh

[57] ABSTRACT

A method of detecting the vapors of particular organic materials, such as narcotic vapors, in which a test plate is provided having a surface coated with an antibody specific for a particular organic material. The test plate is exposed to atmosphere in a region where the presence of the organic material is suspected so that, if vapors of the particular organic material are present, the material will react with the antibody and cause an observable change in the optical properties of the test plate.

20 Claims, No Drawings

METHOD FOR DETECTING ORGANIC VAPORS

BACKGROUND OF THE INVENTION

The present invention relates to methods for detecting the presence of organic vapors and more particularly to the use of antibody-coated test plates for detecting the presence of particular airborne organic material such as the vapors of narcotics.

The problems associated with the proliferation of narcotics need no great elaboration. "Narcotics" as used herein shall be defined broadly to include illicit drugs as defined by laws of the United States and by international convention. The term "narcotics" particularly includes opiates such as opium, morphine and heroin, as well as cannabinol and cocaine. The detection of narcotics is a concern of law enforcement officials. Since narcotics are often highly potent, quantities sufficient to provide numerous doses may be easily concealed.

The concealability of narcotics is especially problematic in law enforcement situations where the presence of drugs is a mere possibility. Customs officials may be constantly alert for narcotics, but the sheer impossibility of searching every package or every suitcase insures that quantities of narcotics will go undetected. If customs officials could know with a certainty when narcotics are in fact present, they could adjust their procedures accordingly.

Significant legal problems may prevent police officials from discovering narcotics even where they strongly suspect the presence of such drugs. Narcotics are often located where police need a warrant to search and, to obtain such a warrant, must be able to show probable cause. The ability to say with a certainty that narcotics are present might aid police in convincing a judge to issue a search warrant.

Animals, particularly dogs, have been employed to detect narcotic odors in the air. Dogs, however, cannot be taken everywhere. Furthermore, dogs are obvious, and an undercover law enforcement official cannot have a sniffing dog with him at all times. It would therefore be desirable to have a simple portable test device which will detect the presence of narcotics in a region before the narcotics are actually located.

Narcotics, as all chemicals, have particular vapor pressures. If vapors of a narcotic can be particularly identified within the atmosphere of a region, the presence of the narcotic may be assumed.

While chemical tests are available for substantially all narcotics to ascertain that a sample is or contains the particular narcotic, identifying their vapors is considerably more difficult. The vapor pressures of many solid substances, including most narcotics, is low and the concentration of molecules in the air will accordingly be low. Any test for vapors of a minimally volatile substance must be highly sensitive. Furthermore, such a test should be highly specific for the material to be identified, particularly when a single test is used to determine its presence. As opposed to a laboratory, where organic compounds to be identified may be isolated and subjected to a battery of tests for identification, a field test for vapors must particularly identify an unisolated compound, preferably in a single test even at low levels and in the possible presence of vapors of other similar compounds.

The high degree of specificity needed to detect vapors of particular organic material is found in biological systems, e.g., the olfactory system of dogs. On a molecular level, certain proteinaceous compounds, such as antibodies found in the immuno-systems of organisms, may be extremely selective and may react with a single compound or at least a very limited class of related compounds.

While antibodies produced by the immuno-systems of organisms generally are specific for particular macromolecules such as foreign proteins, various immunological techniques have been developed to "trick" organisms into producing antibodies which will react with and are specific for many small or medium size organic molecules.

Antibodies, due to their high degree of specificity, have been used to test for the presence of trace amounts of particular organic material, e.g., Lukens and Williams, *Environmental Science and Technology*, 11, pp 292–297 (1977). If antibodies are to be used to detect trace amounts of organic vapors, it is necessary to expose the antibody molecules to the atmosphere in a manner which allows for binding of the particular organic material thereto and in a manner by which the complexing of the antibody and the organic vapor may be definitively observed.

U.S. Pat. No. 4,054,646, issued Oct. 18, 1979, to Giaever, describes a number of test plates for immunological tests by which solutions may be tested for the presence of various immunologically active compounds including antibodies, antigens and haptens (incomplete antigens). The test plates described in U.S. Pat. No. 4,054,646 are glass slides coated with a thin layer of metal which, in turn, is coated by an antibody or an antigen (a chemical to which an antibody specifically binds). When such test plates are submerged in a solution containing the corresponding antigen or antibody, an antigen-antibody complex is formed on the surface thereof which results in a change of the light transmittance or the light reflective characteristics of the test plate. Such test plates make efficient use of antibody or antigen (either of which may be very expensive to produce and/or isolate) by distributing the immunological material (antibody or antigen) over a large surface area to maximize its exposure. The shiny surface of the metal layer is particularly suitable for accentuating changes in the optical properties resulting from the formation of the complex.

The adaption of antibody-coated test plates to the detection of airborne vapors would permit simple quick testing for particular organic material to be done in the field. While antibody-coated test plates have been described, most test plates actually developed are antigen coated plates used to detect antibodies in solution. While antibody-coated plates have been described which test for antigens or haptens in solution, few such antibody-coated test plates have been developed due to problems particular to applying antibodies to test plates in a manner that the antibody remains reactive with the organic material to which it is specific.

Antibodies tend to coat a metal surface in a preferred orientation which may be antithetical to the binding of the antibody to the organic material to which it is specific. Antibodies generally have a large number of active groups aligned in a particular orientation so as to specifically bind with a particular organic material or with a limited class of organic materials. When exposed to a metal surface, these active groups may react with the metal to bind the antibody thereto in a particular alignment. If the active sites necessary to recognize the particular organic material are bound to the metal, the antibody is unable to complex with the organic material.

Immunoglobulin type G antibodies, the type of antibodies found most commonly in the blood of mammals and hence the most easily obtained, have an Fab end which generally contains the binding sites for the particular organic material and an Fc end which generally does not bind to the particular organic material. When type G antibody is applied to a metal surface, the tendancy is for the Fab rather than the Fc end to bind with the metals. Fab-metal binding obscures the sites available for complexing, and, thus, unless the natural tendency for Fab-metal binding is overcome, few binding sites will be available for binding with the organic material. While some Fc-metal binding will occur, the loss of available specific binding sites due to Fab-metal binding is especially problematic in developing test plates for vapor detection where the amount of the particular organic material available for binding is generally far less than is available in solution.

It is a primary object of the present invention to provide a method of detecting the presence of airborne organic material, particularly the presence of narcotic vapors, within a region. It is a further object of this invention to adapt antibody coated test plates to the detection of vapors of particular organic materials.

SUMMARY OF THE INVENTION

The present invention provide a method of detecting the presence of a particular organic material within a region by exposing to the atmosphere of a region a test plate having a surface coated with an antibody for the specific organic material. Changes in light reflectivity and/or light transmittance due to antibody-organic material complex formation on the surface of the plate are observed.

DETAILED DESCRIPTION OF THE INVENTION

Methods of producing antibodies are well known in the art and are hereinafter described merely in sufficient detail for the understanding of the present invention. Antibodies of macromolecules with molecular weights upward of about 140,000, e.g., hepatitis antibodies, are produced by introducing the macromolecule or a macromolecule-producing microorganism or virus into an animal to which the macromolecule is foreign. The immuno defense mechanisms of the organism develop antibodies which specifically bind with the macromolecules (now antigens to the developed antibodies) to neutralize the foreign macromolecules.

Smaller organic molecules in the size range of most narcotics will generally not induce an organism to produce antibodies. Accordingly, small organic molecules must be presented to an organism in a manner which induces the organism to produce antibodies which specifically complex with the small organic molecules, i.e., in a manner which activates the immunological defense systems of the organism.

The immuno systems of organisms respond most readily to large foreign molecules and especially to large foreign protein or protein based molecules. Small molecular weight chemicals, which do not activate the immunological systems of organisms, may do so if conjugated with large molecules such as large proteins. The small organic moiety which is conjugated with the large molecule is referred to as a hapten. The hapten-large molecule conjugate may induce the organism to produce antibodies which are specific either to the entire conjugate or to the hapten moiety alone. Generally, some fraction of the antibody induced by such a conjugate will be active with the hapten moiety. Thus antibodies may be produced which are highly selective for particular low molecular weight compounds.

A preferred method for producing antibodies of small or medium sized organic compounds is described by Williams and Lukens, "The Application of Immunological Techniques to the Detection of Organic Contaminants of Environmental Concern" presented June 8, 9 and 10, 1976 at the University of Missouri 10th annual conference on Trace Substances in Environmental Health. Briefly stated, organic molecules are bound to mammalian serum protein, such as serum albumin, by subjecting a solution of the organic material and the protein to ionizing radiation. The conjugates thereby produced are injected into a mammal other than that from which the serum protein is derived. For example, an antigen, comprised of bovine serum albumin conjugated to opium, may be injected into rabbits which produce antibodies to resist the foreign proteinaceous substances. While the opium moiety by itself is not capable of inducing antibody production, a portion of the rabbit antibody induced by the albumin-opium conjugate, has active sites which bind to unconjugated opium. By the method described by Williams and Lukens, antibodies are produced for various illicit substances such as opium, cannabinol, heroin, cocaine and morphine.

Conjugates to induce antibody production may alternatively be obtained by ordinary chemical means such as that described in U.S. Pat. No. 3,064,228 issued Dec. 20, 1977 to Grass pertaining to morphine antibodies.

To produce the test plates of the present invention, glass slides are prepared for indium coating by extensive cleaning. The slides are cleaned with detergent and then rinsed with distilled water. Subsequently, the slides are washed with reagent grade acetone and ethanol. After drying, the slides are subjected to argon plasma under vacuum for 15 minutes.

Indium is vapor deposited on the slides by tungsten filament evaporation of indium metal from a tantallum boat in a vacuum of about $10^{-5}$ torr. The slide is coated with indium to a thickness of between about 50 and about 1000 angstroms and preferably between about 100 and about 200 angstroms (as may be measured by a Sloan thickness monitor). Such thin layers of indium metal allow light transmittance therethrough and permit test plates to be read either by changes of light transmission or light reflection. Thicker layers of indium metal are suitable if only light reflective properties are to be examined.

The antibodies are applied to the indium coated slide either by dipping the slide in an appropriate antibody-containing solution or by placing a drop of the solution on the slide. The concentration of antibody is not considered particularly critical as a monolayer of antibody will deposit on the metal layer given sufficient time since active groups in the antibody bind with the metal. Once a monolayer is formed, further antibody will not deposit on the metal coated slide.

As hereinbefore mentioned, immunoglobulin G antibodies tend to prefer Fab-metal bindings. In order that sufficient Fab ends are exposed for complexing with the particular organic material to be detected, conditions are adjusted so that Fc-metal binding is preferred or is at least reasonably competitive with Fab-metal binding. The Fab end has a predominance of active amino groups while the Fc end has a predominance of reactive carbonyl groups. Deactivating the amino group of the Fab end and activating the carbonyl groups of the Fc end increases Fc-metal binding. This may be accomplished by making the antibody solution slightly basic by adjusting the pH to between about 8 and about 13. Preferably the solution has an ionic concentration of $K^+$ of between about 0.001 M and about 0.1 M and most preferably in amounts of about 0.03 M. Appropriate conditions may induce upward of 50% of the type G antibody to form Fc-metal bonds so that at least about 50% of the antibody molecules are in correct orientation for binding with the particular organic material.

The test plate, with the monolayer of antibody coated on the indium layer, has a shiny, mirror-like appearance. When an organic material, particular to an antibody, complexes with the antibody, the mirror surface becomes noticably clouded. The clouding of the test plate, caused by complexing of the organic material with the antibody, may be most easily observed by comparing an exposed test plate side by side with a non-exposed test plate.

The presence of vapors of an organic material is detected by the change in optical properties of the test plate resulting from the surface area of the test plate becoming coated with the antibody-organic material complex. In order that an observable change in optical properties occur, a sufficient percentage of the surface area of the test plate must become covered with molecules of the organic material complexed to the antibody. The percentage of the surface which must become coated with molecules of the organic material will depend, of course, on the sensitivity of the optical measuring methods. For test plates which are intended for use in the field and are to be read by the naked eye, the light reflective properties of the test plate will be noticeably affected if at least about 5% of the surface area is covered with molecules of the complexed organic material. If the test plates are to be read by a spectrophotometer, less of the surface area need be covered by molecules of the organic material.

An estimation of the surface area of a test plate which will become covered by molecules of an organic material will take into account the surface area of the plate covered by each antibody molecule, the surface area of the plate covered by each molecule of the organic material complexed with the antibody, the number of binding sites per molecule of antibody, the percentage of antibody molecules bound to the metal so as to have exposed binding sites, and the degree of saturation of the exposed antibody sites.

The test plates, which are coated by a monolayer of antibody, may have 50% or more of the antibody in correct alignment to bind with molecules of the particular organic material. Antibody molecules of the immunoglobulin G type have a molecular weight of about 140,000 and cover about 1,000 square angstroms of the surface area of the test plate. Cannabinol and morphine, exemplary of organic material to be tested for, have molecular weights in the 300–400 range and cover a surface area of about 100 square angstroms. Though the molecular weights of the antibodies are generally much larger than the molecular weights of the organic molecules which the test plates are intended to detect, the protein chains of the antibodies are repeatedly folded, and the smaller organic molecules are generally flatter, and accordingly, the descrepancy in molecular weights is not reflected to the same degree in the amount of surface area covered by the molecules. As there are two binding sites per type G antibody molecule, up to 10% of the surface area of the test plate (with 50% exposed sites) may be covered with the bound organic material when all of the active antibody is complexed therewith. Accordingly, if the test plates become about one-half saturated, the organic material causes sufficient clouding of the mirror surface so as to be noticably changed when observed by the naked eye.

The presence of airborne organic material is best detected in a humid environment. This is especially true if the organic material has a very low vapor pressure. If the organic material is soluable in water, the water vapor will carry the organic material, thereby increasing the amount of the organic material which may be carried by the air. Additionally, as is to be expected, since antibody-organic material complexing naturally takes place in the aqueous environment of a living organism, water molecules may enter into the complexing reaction. The test plates of the present invention are most effective when the relative humidity is at least about 30%, but longer exposure times may be used to develop the test plates in dryer environments. In a closed, controlled environment, such as a custom house, the air may be humidified to about 30% relative humidity to facilitate narcotics detection, but the natural ambient humidity will generally be sufficient.

At room temperature, cannabinol has a vapor pressure of 0.0031 atmosphere so that, when staturated, air will contain about $10^{17}$ molecules per cc. Morphine which has about one-tenth the vapor pressure of cannabinol will saturate the air with about $10^{16}$ molecules per cc of air. The test plates are sufficiently sensitive to detect organic materials which are present in the atmosphere in the range of about $10^{11}$ molecules per cc of air, and generally the test plates will be capable of detecting organic materials with a vapor pressure of at least about $3\times10^{-9}$ atmosphere. While the effectiveness of the tests will depend on such factors as temperature, humidity, vapor pressure of the particular substance, ventilation, and time of exposure, the sensitivity of the test is sufficient to permit organic materials such as narcotics to be detected under far less than ideal conditions.

When read by the naked eye, the test may depend on the ability of the tester to notice subtle clouding and/or change of color of the test plate. In order to do so a control should be provided.

One way to provide a control is to shield a portion of the test plate from exposure with a cover of some type while another portion is exposed to the atmosphere. For example, a test plate may be provided with a pair of transparent cover slips. One of the coverslips is removed to expose a portion of the test plate to the atmosphere while a shielded portion remains protected by the other coverslip. For accurate visual comparison, the removed coverslip is replaced over the exposed portion before the test plate is read. Alternatively, a portion of the test plate may be pre-reacted to saturate a portion of the test plate with the organic material. Development of similar cloudiness or color change on the remaining portion would indicate the presence of the particular organic material in the region being monitored. A drawback to this method is that the test portion of the test plate may have to become nearly saturated before the test would be definitive.

A further alternative is to provide a standard, preferably a standard with a plurality of portions of different optical properties, to compare with the test plate before and after exposure to the atmosphere of a region. Such a standard may be provided integral with the test plate.

In a controlled region such as a custom house, or in situations where the test plate may be returned to the laboratory for further analysis, the use of optical equipment, i.e. a spectrophotometer, will increase the sensitivity of the test by detecting very subtle changes in light reflectivity and/or light transmittance of the test plate.

In situations where further analysis is permitted, procedures which employ radioactive or fluorescent materials may be used to enhance the sensitivity of the test plates. For example, test plate of which a portion has been exposed to atmosphere may be dipped in a solution of a radioactive form of the organic material or in a solution of the particular organic material which is carried by a fluorescent material. The exposed and non-exposed portions of the plate are thereafter compared for radioactivity or fluorescence. If the exposed portion of the test plate has complexed with airborne narcotics, it has fewer sites available for complexing with radioactive or fluorescent antigen and thus exhibit less radioactivity or fluorescence than the non-exposed portion after developing.

EXAMPLE I

An aqueous solution is prepared containing 20 mg of bovine serum albumin per ml and 0.4 mg. of cannabinol per ml at pH 7.0. The solution is subjected to a 4 megarad dose of ionizing radiation by bombarding it with 10 MeV electrons from a electron linac. The resulting irradiated mixture is dialyzed for 24 hr. against 15 M NaCl, 0.015 M phosphate, at pH 7.0 and 4° C.

The dialyzed solution is made up to 1.5 ml in 0.15 M NaCl and mixed 1:1 with complete Freund's adjuvant.

Rabbits are injected with 0.2 ml of the dialyzed solution at each of 2 sites. At 8 and 16 weeks the rabbits are given booster inoculations at 1/50th of the original immunogen concentrations.

Ten days after each innoculation, the rabbits are bled (40 ml per rabbit), the serum separated from the blood clot, and a globulin fraction obtained by $(NH_4)_2SO_4$ precipitation of the serum.

The globulin fraction is electrophoresed on a cellulose acetate plate in pH-8-electrolyte buffer to isolate the immunoglobulin G fraction. A cannabinol sensitive fraction is obtained therefrom by the immuno-sorbtion technique as described in Dandliker and Saussure, *Immunochemistry*, Vol. 5, 357–365, 1968. KOH is added to the cannabinol fraction to a concentration of 0.03 M.

A glass microscope slide, covered on one surface with vapor-deposited indium to a thickness of 200 angstroms, is submerged in the solution of cannabinol antibody overnight at 4° C. to insure that the plate is coated by a monolayer of the antibody.

The test plate is dried, and two adjacent portions are each covered with a transparent cover slip.

In a closed room wherein the temperature is about 21° C. and the relative humidity is measured at 37%, one-half gram of marijuana (i.e. about one marijuana cigarette) is exposed to the atmosphere for ½ hour.

One of the coverslips is removed and the plate is exposed to the atmosphere about 8 feet from the marijuana sample for 5 minutes, after which the cover slip is replaced. A control plate is similarly exposed to atmosphere free of cannabinol. The exposed portion of the test plate is cloudier than the unexposed portion as may be observed by visual inspection. The control plate exhibits no difference between the exposed and unexposed portions.

The light transmittances of the exposed and unexposed portions of the test and control plates are measured with a McBeth-Ansco optical densitometer with the following results:

| TEST PLATE | | CONTROL PLATE | |
|---|---|---|---|
| EXPOSED PORTION | UNEXPOSED | EXPOSED | UNEXPOSED |
| 0.315 | 0.340 | 0.344 | 0.344 |

The above conditions are exemplary of conditions which may be present in a room of a customs house wherein packages are received for possible inspection. A package containing marijuana or hashish will sit around the room for a sufficient period to permeate the room with cannabinol vapors. Upon a positive test, the customs officials may search packages until the narcotic is found. On the other hand, a negative test will save the officials considerable time. While customs officials are unlikely to be interested in discovering a single marijuana cigarette, the efficiency of the test is demonstrated by its sensitivity to small amounts.

EXAMPLE II

Antibody for morphine are produced according to the procedure described in Gross, U.S. Pat. No. 4,064,288. A test plate is prepared according to the above-described methods. Two adjacent portions of the test plate are covered with transparent coverslips.

2 grams of morphine are left exposed in a closed automobile for ½ hr. at 12° C. at 46% relative humidity. A window is rolled down, one of the coverslips is removed from the test plate, and the test plate is held about ½ meter from the open window for 1½ minutes. The exposed portion of the test plate is visably clouded as compared to the unexposed portion.

The above test is exemplary of the use to which a test plate may be put by a police officer in the field. An officer may detect a suspicious vehicle, but have no particular cause to search the car. The officer may apprehend the vehicle and, while talking to the driver, examining the driver's license and otherwise passing time, the officer may be holding test plates for various narcotics in close proximity to the open window of the car. The officer may take the plates back to his car for examination, and, if a plate is positive, he may take further appropriate action.

EXAMPLE III

A cannabinol test plate is prepared as per Example I.

Ten grams of marijuana are placed in a room and exposed to the atmosphere for two hours. The temperature in the room and directly thereoutside is about 19° C. and the relative humidity is about 27%. The test plate is placed on the floor directly outside the bottom of a door to the room which hangs about ¼ inches from the floor and left there for 20 seconds. The test plate is placed in a vapor-proof bag for transportation to the laboratory. The test plate is placed in a solution 0.01 M in cannabinol bound to a fluorescent carrier. After 10 minutes the test plate is removed, washed throughly with distilled water and held under a UV light source. The unexposed portion is visably more fluorescent than the exposed portion.

The above test is to simulate conditions which may confront a police officer who must go before a judge to request a search warrant. The police officer may have good reason to suspect that narcotics are being bought and sold in a certain apartment but have no particular evidence which would support the granting of a search warrant.

The police officer may walk by the door of an apartment, deposit a test plate on the floor and return several seconds later to retrieve the test plate. While the narcotic vapor which eminates under the door may be limited, and while the officer may wish to hurry out of a potentially dangerous location, there is plenty of time back at the laboratory to develop the test plate with fluorescent carrier. A positive result of a test which is highly specific should help a police officer convince a judge that a search warrant should be issued.

While the invention has been described according to certain preferred embodiments, modifications obvious to one skilled in the art may be made without departing from the teachings of the present invention.

Various features of the invention are set forth in the following claims:

We claim:

1. A method of detecting the presence of a particular organic material within a region comprising;
   providing a test plate having a surface coated with an antibody for a specific organic material;
   exposing said test plate to the atmosphere of a region suspected of carrying vapors of said organic material;
   and,
   observing changes in optical properties of said surface indicating the presence of said organic material.

2. A method according to claim 1 including shielding a first portion of said surface from exposure while exposing a second portion of said surface to the atmosphere of the region and comparing the optical properties of said first and said second portion.

3. A method in accordance with claim 1 including;
   pre-exposing a first portion of said surface to said organic material;
   exposing a second portion of said surface to the atmosphere of the region; and,
   comparing the optical properties of said first and said second portions.

4. A method according to claim 1 wherein said changes are observed by comparing reflective properties of said test plate.

5. A method according to claim 1 wherein said changes are observed by comparing light transmittance properties of said test plate.

6. A method according to claim 1 wherein said test plate has a surface coated with an antibody for a narcotic.

7. A method according to claim 1 wherein said test plate has a surface coated with a antibody specific for a narcotic selected from the group consisting of opium, morphine, heroin, cannabinol and cocaine.

8. A method according to claim 1 also including the step of humidifying the air of said region to achieve at least about a 30% relative humidity.

9. A method according to claim 1 wherein said antibody is specific for an organic material having a vapor pressure of at least about $3 \times 10^{-9}$ atmosphere.

10. A method according to claim 1 further comprising;
    exposing a first antibody-coated portion of said test plate to the atmosphere of a region;
    shielding a second antibody-coated portion of said test plate to the atmosphere of the region;
    introducing said first and said second portion to a solution containing said specific organic material bound to a fluorescent carrier; and
    comparing the fluoresence of said first portion and said second portions.

11. A method according to claim 1 further comprising;
    exposing a first antibody coated portion of said test plate to the atmosphere of a region;
    shielding a second antibody-coated portion of said test plate to the atmosphere of the region;
    introducing said first and said second portion to a solution of a radioactive form of said specific organic material; and,
    comparing the radioactivity of said first and said second portions.

12. A test plate for detecting vapors of a specific airborne organic material comprising:
    a substrate;
    a layer of metal on said substrate; and
    a monolayer of an antibody which complexes with a particular organic material having a vapor pressure of at least about $3 \times 10^{-9}$ atmosphere bonded to said layer of metal in such manner that said monolayer contains sufficient active binding sites available for binding with said particular organic material that when substantially all of said binding sites are complexed with molecules of said organic material, said molecules of said organic material cover at least about 5% of the surface area of said test plate so that when said test plate is exposed to atmosphere which contains vapors of said organic material, molecules of said organic material will complex with said antibody thereby changing the optical properties of said test plate.

13. A test plate according to claim 12 wherein said antibody is specific for a particular narcotic.

14. A test plate according to claim 12 wherein said antibody in specific for particular narcotics selected from the group of opium, heroin, morphine, cannabinol and cocaine.

15. A test plate according to with claim 12 wherein said antibody is of the immunoglobulin G type.

16. A test plate according to claim 12 wherein cover means is provided to shield a first portion of said test plate from exposure to atmosphere when a second portion is exposed to atmosphere.

17. A test plate in accordance with claim 12 wherein, a first portion of said test plate is pre-exposed to a solution of said particular organic material to react with said organic material and change the optical properties of said first portion, and a remaining second portion is unexposed to said solution so that said first and said second portions of said test plate may be compared after exposure of said second portion to the atmosphere of a region.

18. A test plate according to claim 12 wherein said test plate also includes a standard having a plurality of portions of different optical properties to which the optical properties of said test plate may be compared before and after exposure to atmosphere.

19. A method of preparing a test plate for the detection of airborne vapors of a particular organic material including;
providing a substrate;
coating said substrate with a layer of metal;
coating said layer of metal with a monolayer of an immunoglobin type G antibody specific for said particular organic material;
the improvement comprising;
applying said antibody to said test plate by exposing said layer of metal to a solution of said antibody, which solution has a pH of between about 8 and about 13, whereby said monolayer provides sufficient available binding sites to complex with an optically detectable amount of airborne vapors of said organic material.

20. A method according to claim 19 wherein the ionic concentration of $K^+$ is between about 0.001 M and about 0.1 M.

* * * * *